(12) United States Patent
Kantor

(10) Patent No.: US 11,400,007 B2
(45) Date of Patent: Aug. 2, 2022

(54) DEVICE FOR OPTIMAL AIRWAY OPENING

(71) Applicant: INOVYTEC MEDICAL SOLUTIONS LTD., Hod Hasharon (IL)

(72) Inventor: Ehud Kantor, Hod Hasharon (IL)

(73) Assignee: INOVYTEC MEDICAL SOLUTIONS LTD., Hod Hasharon (IL)

( * ) Notice: Subject to any disclaimer, the term of this patent is extended or adjusted under 35 U.S.C. 154(b) by 738 days.

(21) Appl. No.: 16/313,201

(22) PCT Filed: Jul. 2, 2017

(86) PCT No.: PCT/IL2017/050738
§ 371 (c)(1),
(2) Date: Dec. 26, 2018

(87) PCT Pub. No.: WO2018/008016
PCT Pub. Date: Jan. 11, 2018

(65) Prior Publication Data
US 2019/0151180 A1    May 23, 2019

Related U.S. Application Data

(60) Provisional application No. 62/358,006, filed on Jul. 3, 2016.

(51) Int. Cl.
*A61G 13/12* (2006.01)
*A61G 1/04* (2006.01)
(Continued)

(52) U.S. Cl.
CPC .............. *A61G 13/121* (2013.01); *A61F 5/56* (2013.01); *A61G 1/04* (2013.01); *A61G 7/072* (2013.01); *A61B 90/14* (2016.02); *A61M 16/01* (2013.01)

(58) Field of Classification Search
CPC .. A61G 13/121; A61G 13/12; A61G 13/1215; A61G 13/129; A61G 15/12;
(Continued)

(56) References Cited

U.S. PATENT DOCUMENTS 2,452,816 A * 11/1948 Wagner .................. A61G 13/12
5/636
4,266,759 A * 5/1981 Liebman .............. A61H 31/008
5/632
(Continued)

FOREIGN PATENT DOCUMENTS

CA       2916907 A1    12/2014
CN    101495170 A      7/2009
(Continued)

OTHER PUBLICATIONS

International Search Report for PCT/IL2017/050738; dated Sep. 28, 2017 (5 pages).
(Continued)

*Primary Examiner* — Erin Deery
*Assistant Examiner* — Daniel A Miller
(74) *Attorney, Agent, or Firm* — Roach, Brown, McCarthy & Gruber, P.C.; Kevin D. McCarthy

(57) ABSTRACT

Described is a wearable device that combines a mechanism which is configured for modifying a head angle of the subject when in the supine position in order to achieve a head tilt position and a mechanism for causing a forward movement of the mandibles in order to obtain an optimal open airway in a subject. Embodiments of the device are configured to be attached to a bed, stretcher, or other flat surface.

12 Claims, 4 Drawing Sheets

(51) Int. Cl.
*A61G 7/07* (2006.01)
*A61F 5/56* (2006.01)
*A61M 16/01* (2006.01)
*A61B 90/14* (2016.01)

(58) Field of Classification Search
CPC .......... A61G 15/00; A61G 1/04; A61G 7/072; A61F 5/56; A61B 90/14; A61M 16/01
USPC ................ 602/17, 18; 128/869, DIG. 23
See application file for complete search history.

(56) References Cited

U.S. PATENT DOCUMENTS

| | | | |
|---|---|---|---|
| 5,524,639 | A | 6/1996 | Lanier et al. |
| 6,282,734 | B1 * | 9/2001 | Holberg ............... A61G 7/1026 5/81.1 HS |
| 6,289,558 | B1 * | 9/2001 | Hammerslag ............ A43B 5/16 24/68 SK |
| 7,055,524 | B1 | 6/2006 | Taimoorazy |
| 7,350,250 | B2 | 4/2008 | Froelich |
| 9,937,312 | B2 | 4/2018 | Kwok et al. |
| 2005/0160532 | A1 * | 7/2005 | Froelich ................. A61G 13/12 5/622 |
| 2011/0036355 | A1 | 2/2011 | Farnum |
| 2011/0253150 | A1 * | 10/2011 | King .................... A61G 13/121 128/845 |
| 2012/0097158 | A1 * | 4/2012 | Matalon .............. A61M 16/021 128/202.18 |
| 2012/0101417 | A1 | 4/2012 | Joseph |
| 2016/0101008 | A1 * | 4/2016 | Haworth ............ A61G 13/1215 128/845 |

FOREIGN PATENT DOCUMENTS

| | | | |
|---|---|---|---|
| CN | 105031789 A | 11/2015 | |
| CN | 205055110 U | 3/2016 | |
| GB | 1290523 A | * 9/1972 | ............. A61G 13/12 |
| GB | 1290523 A | 9/1972 | |
| JP | 2010148927 A | 7/2010 | |
| JP | 5615849 B2 | 10/2014 | |
| WO | 2015025319 A1 | 2/2015 | |

OTHER PUBLICATIONS

Written Opinion of the International Searching Authority for PCT/IL2017/050738; dated Sep. 28, 2017 (5 pages).
Chinese office action for Chinese application No. 201780049607.0; transmitted on Sep. 22, 2020; 9 pages and a machine translation.
Communication and Supplementary European Search Report for European application No. 17823759.0, dated Jun. 5, 2020 (11 pages).

* cited by examiner

DEVICE FOR OPTIMAL AIRWAY OPENING

FIELD OF THE INVENTION

The invention is from the field of medical devices. Specifically the invention relates to devices for opening an airway in a patient.

BACKGROUND OF THE INVENTION

Airway obstruction is a common and potentially devastating complication in certain medical conditions such as post-surgery, apnea, trauma, airway obstruction and more.

The most frequent cause of airway obstruction is the loss of pharyngeal tone in an unconscious, sedated or obtunded patient. When the muscles of the tongue and mouth floor relax, the tongue lies close to or on the back wall of the oropharynx. The epiglottis may obstruct the glottic opening or seal against the back wall of the pharynx, as well.

All invasive methods to maintain an open airway involve devices that are inserted into the airway and mechanically supply an open tube aimed to maintain an open airway. There are several non-invasive positioning maneuvers known in the art which can be performed to relieve the soft tissue obstruction and improve air flow. One non-invasive mean to protect the airway in an airway obstructed patient is by pushing the jaw forward in what is known in the art as a "Jaw thrust maneuver" in which the mandibles are pushed forward to prevent backward collapse of the mandible and suffocation.

Another important factor for obtaining an open airway is the angle of the patient's neck. It is important to prevent the head of the treated individual from assuming unwanted positions which may not fully support an open airway or may even obstruct the airway as often happens when a pillow is placed behind the head. In order to have optimal opening of the airway there is a need to tilt the head of the subject backwards in a suitable angle. Tilting of the head results in neck extension which opens any obstruction caused by relaxation of the soft tissues of the oropharynx and thus ensures an open airway.

Optimal airway opening is obtained through a delicate balance between the two positioning maneuvers described above. Therefore, there is an unmet need for a device which is capable of simultaneously performing both actions of head tilt and jaw thrust maneuver.

During this action in order to better control the airway opening on a syncope or pre-syncope patient in a supine position it is advantageous to fixate the patient's head. The fixation of the head should be done when the optimal airway opening is achieved. The importance of maintaining the head in a fixed position is in order to obtain control of the spine after orthopedic surgery or trauma, to allow optimal intubation in a pre and during anesthetic surgery and to maintain the optimal position for the airway opening.

It is therefore a purpose of the present invention to provide a device which is capable of simultaneously performing both actions of head tilt and jaw thrust maneuver.

It is another purpose of the invention to provide an airway support device for post anesthesia surgeries, recovery rooms, and sedation procedures overcoming the common airway obstruction and potentially devastating complications in the post operative period.

Further purposes and advantages of this invention will appear as the description proceeds.

SUMMARY OF THE INVENTION

The invention is a wearable device for opening an airway in a patient The device comprises: a semi-rigid neck support that is positioned behind the neck and is configured to support the neck of the subject, a mechanism configured for modifying a head angle of a subject when in the supine position in order to achieve a head tilt position, and a mechanism configured for causing a forward movement of the mandibles in order to obtain an optimal open airway.

In embodiments of the device modifying the head angle of the subject and causing a forward movement of the mandibles of the subject can be performed either separately or simultaneously.

In embodiments of the device the mechanism configured for modifying a head angle of a subject comprises:
 a) a flexible primary strap configured to be worn on a head of a subject, wherein the primary strap passes over the forehead or over the nose bridge of the subject and the neck of the subject;
 b) a head tilt mechanism located on one side of the head of the subject, the head tilt mechanism comprising:
  i) a pulley to which a first end of the primary strap is firmly affixed; and
  ii) a rotatable handle mechanically linked to the pulley;
wherein:
 a') the head tilt mechanism is firmly affixed to the neck support;
 b') a second end of the primary strap is firmly affixed to the neck support on the side of the head of the subject opposite to the side at which the head tilt mechanism is affixed to the neck support;
 c') the handle is configured such that rotating it in one of a clockwise or counterclockwise direction exerts a force via a mechanical connection on the pulley wrapping the end of the primary strap around the pulley effectively applying a force via the primary strap that pulls the head downwards and rotating the handle in the opposite direction unwraps the primary strap from around the pulley effectively reducing the force that the primary strap exerts on the head allowing the head to move upwards.

In embodiments of the device the device the mechanism configured for modifying a head angle of a subject comprises a secondary strap that is connected to the primary strap and runs over the top of the head.

In embodiments of the device the head tilt mechanism comprises a locking mechanism.

In embodiments of the device mechanical connection between the handle and the pulley is either a belt or a gear train.

In embodiments of the device the mechanism configured for causing a forward movement of the mandibles comprises:
 a) two drive mechanisms the lower ends of which are affixed to the neck support on either side of a head of a subject;
 b) a shaft that passes through both of the drive mechanisms;
 c) a handle that is affixed to one end of the shaft;
 d) gears that link the drive mechanisms to the shaft;
 e) two elongated members, one projecting upwards from each drive mechanism, the elongated members configured to be raised or lowered in relation to the neck support;
 f) two mandible engaging elements each configured to match the shape of the mandible on a different one of the sides of the head of the subject;

wherein:
i) each of the two mandible engaging elements is pivotably attached to the upper end of a different one of the two elongated members; and
ii) The handle is configured such that rotating it clockwise or counterclockwise raises or lowers both of the elongated members, thereby pushing the mandible engaging elements upwards or lowering them to move the mandible forwards of backwards.

In embodiments of the device the elongated members are either screws or racks from rack and pinion gear assemblies.

In embodiments of the device the distance between the two drive mechanisms can be adjusted according to the dimensions of the head of the subject.

Embodiments of the device the mechanism configured for causing a forward movement of the mandibles comprise a locking mechanism.

Embodiments of the device are configured to be attached to both a head of a subject and to a bed, stretcher, or other flat surface.

In embodiments of the device the neck support comprises connectors configured to attach the device to anchorage points on the bed, stretcher, or other flat surface.

In embodiments of the device the handle of the mechanism configured for modifying a head angle of a subject and the handle of the mechanism configured for causing a forward movement of the mandibles can be rotated either manually or by a motor.

Embodiments of the device are configured to react to a state of respiratory emergency by automatically opening an airway through activation of one or both of the mechanism configured for modifying a head angle of a subject and the mechanism configured for causing a forward movement of the mandibles in response to measurements of the subject's condition made by sensors configured to evaluate the state of respiration of the subject.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

The present invention is a wearable device for opening an airway in a patient. More specifically the device of the present invention combines a mechanism which is configured for modifying a head angle of the subject when in the supine position in order to achieve a head tilt position (also known herein as a head tilt mechanism), and a mechanism for causing a forward movement of the mandibles (also known herein as a jaw thrust mechanism) in order to obtain an optimal open airway. Head tilt and jaw thrust can be performed either separately or simultaneously.

Figure 1B:
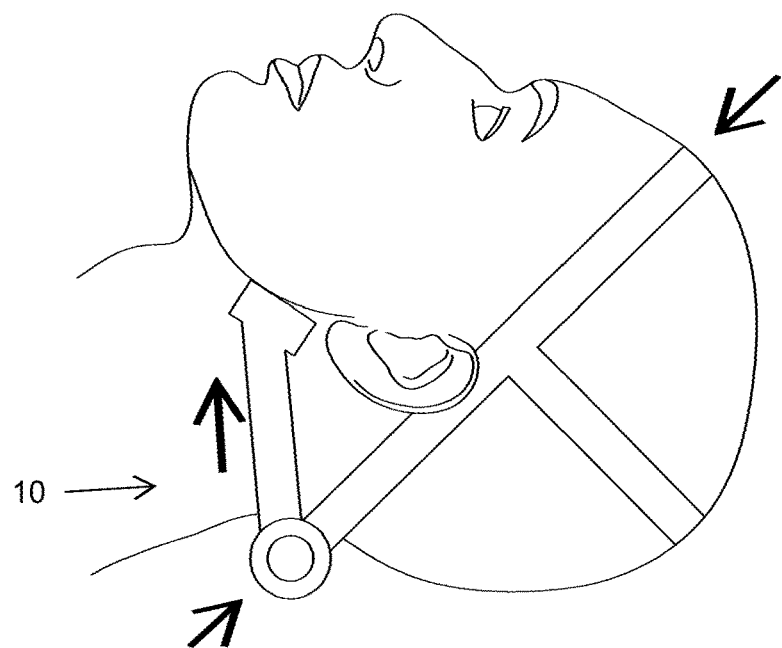
FIG. 1B schematically shows the direction of the forces exerted on the head of a subject by the device of FIG. 1A when the device is activated to simultaneously carry out head tilt and jaw thrust maneuvers.
Figure 1A:
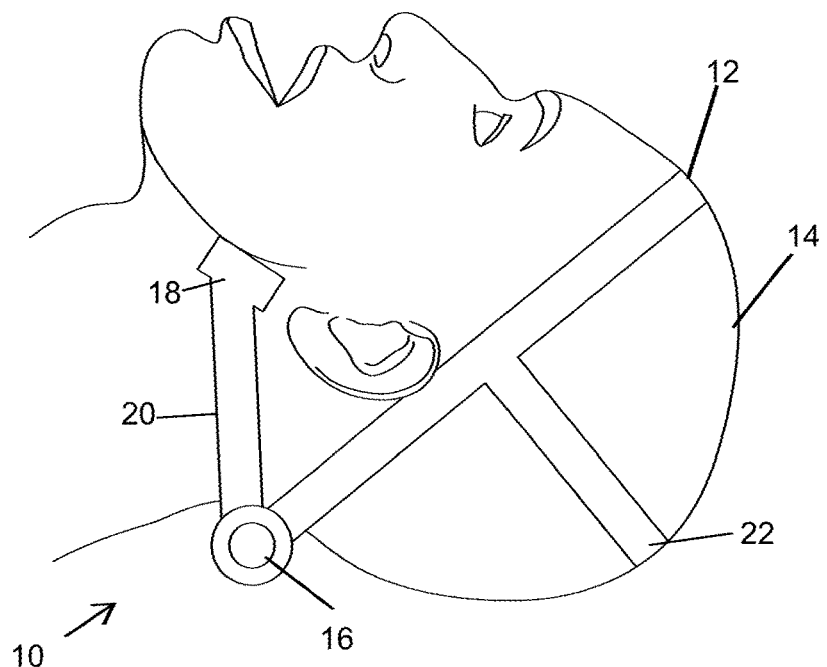
FIG. 1A schematically shows an embodiment of the device.

An embodiment of the device is schematically shown in FIG. 1A. Device 10 comprises a flexible primary strap 12 configured to be worn on the head 14 of a subject passing over the forehead and the neck as shown in FIG. 1A. One side of primary strap 12 is connected to a head tilt mechanism, which will be described in detail herein below. The head tilt mechanism is attached to a semi-rigid element which is positioned behind the neck and is configured to support the neck (hereinafter "neck support" 16). The device 10 may include a secondary strap 22 connected to the primary strap 12 and running over the top of the head 14 to improve the attachment of the device 10 to the head 14.

Mandible engaging elements 18 configured to match the shape of the mandibles are pivotally connected on both sides of the head to components of a jaw thrust mechanisms 20, which are affixed to the neck support 16. In embodiments of the device each of the mandible engagement elements 18 can be fixed to the mandible by stickers or vacuum. The jaw thrust mechanisms 20 are configured to move the mandible engaging elements 18 forward in order to perform a jaw thrust maneuver. Embodiments of the neck support 16, the head tilt mechanism and the jaw thrust mechanism will be described in detail herein below.

The arrows in FIG. 1B schematically show respectively the directions of the forces exerted by primary strap 12, neck support 16, and mandible engaging elements 18 on the head 14 and lower jaw of the patient when device 10 of FIG. 1A is activated to simultaneously carry out head tilt and jaw thrust maneuvers.

In another embodiment of device 10 the primary strap 12 passes over the nose bridge and the neck of the subject instead of over the forehead as shown in FIGS. 1A and 1B.

Figure 2:
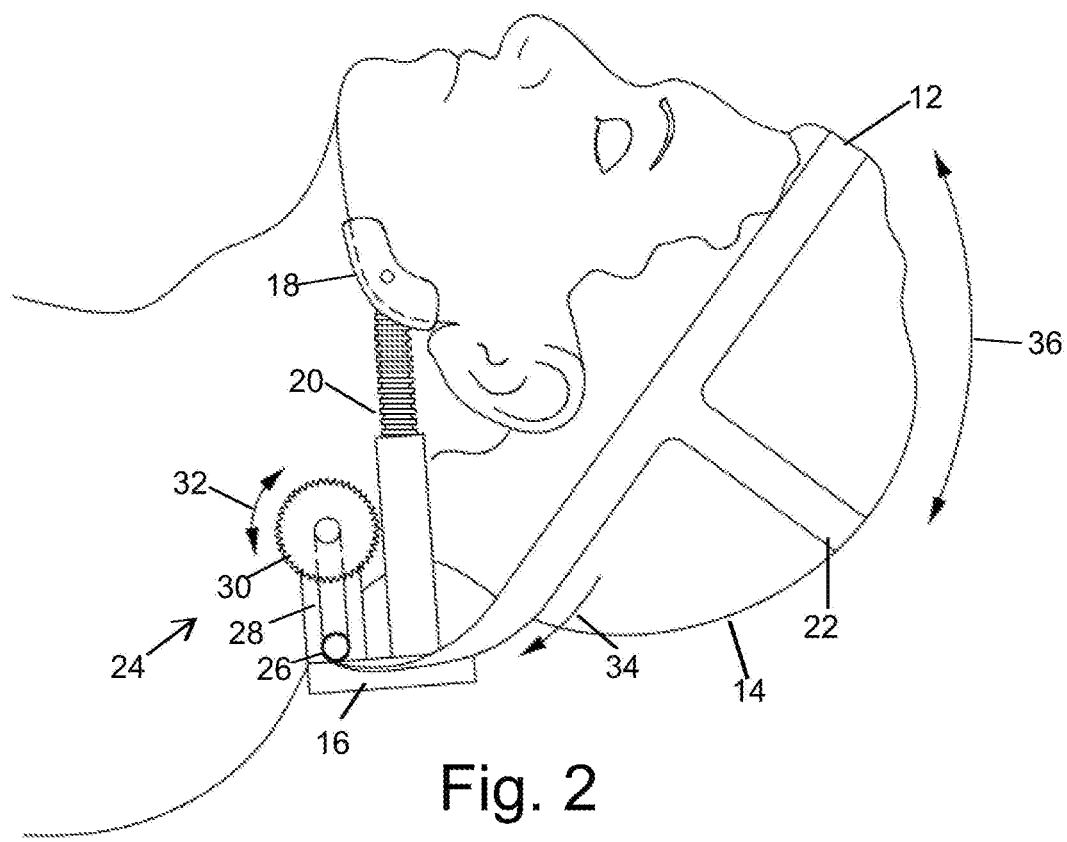
FIG. 2 is a schematic view from the left side of the head 14 of the subject with the device of FIG. 1A attached.
Figure 3:
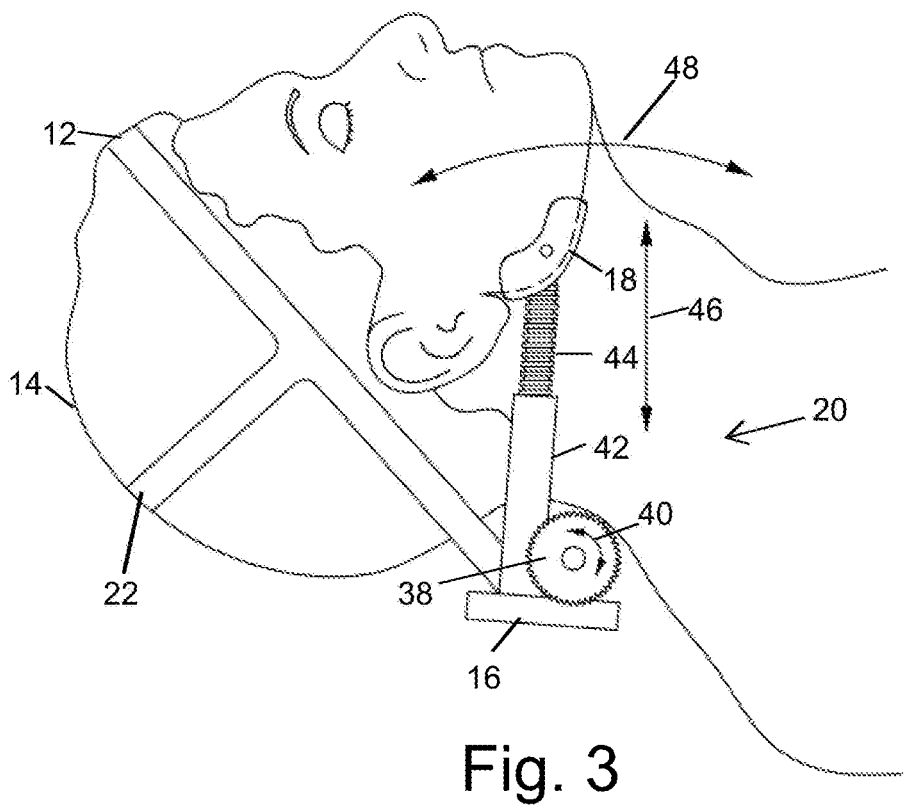
FIG. 3 is a schematic view from the right side of the head 14 of the subject with the device of FIG. 1A attached.
Figure 4:
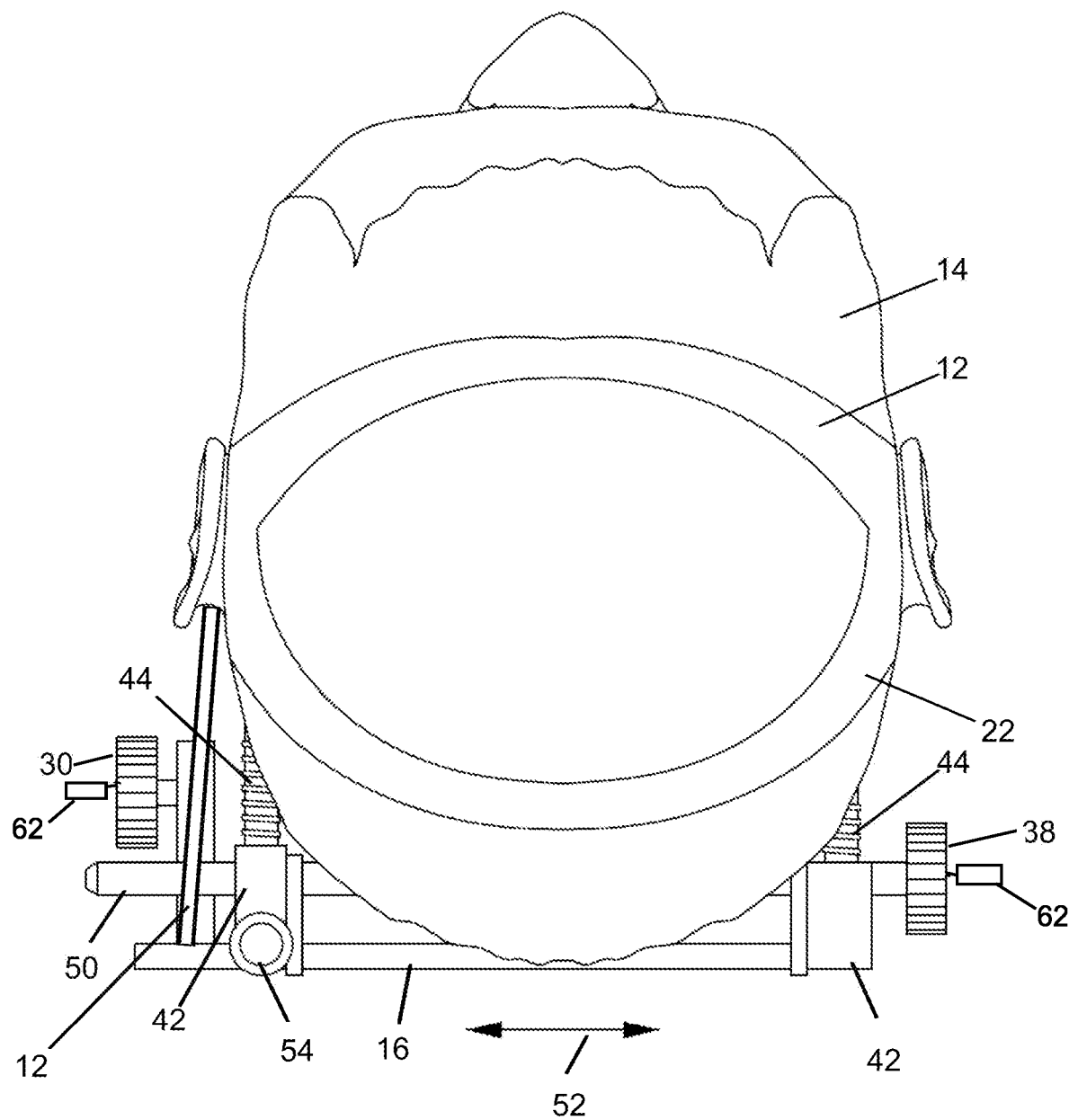
FIG. 4 is a schematic view from the back of the head 14 of the subject with the device of FIG. 1A attached.

FIG. 2 is a schematic view from the left side, FIG. 3 is a schematic view from the right side, and FIG. 4 is a schematic view from the back showing the device of FIG. 1A attached to the head 14 of a subject.

FIG. 2 illustrates how the head tilt mechanism operates to cause head 14 to tilt up and down in the direction shown by arrow 36. The end of primary strap 12 on the right side of head 14 is firmly affixed to neck support 16. The end of primary strap 12 on the left side of head 14 is firmly affixed to pulley 26. An axel of pulley 26 is connected by belt 28 to the axle of rotatable handle 30, which can be rotated clockwise or counterclockwise as shown by arrow 32. Rotating handle 30 in the clockwise direction pulls the end of primary strap 12 in the direction shown by arrow 34 and wrapping the end of around of primary strap 12 around pulley 26 effectively applying a force via primary strap 12 that pulls head 14 downwards. Rotating handle 30 32 counterclockwise unwraps primary strap 12 from around pulley 26 effectively reducing the force that primary strap 12 exerts on the head allowing the head to move upwards. The head tilt mechanism comprises a locking mechanism, e.g. a pin or pawl, which maintains the head at an optimal angle. In other embodiments a gear train can replace belt 28 that transfers force from handle 30 to pulley 26. Handle 30 can be rotated either manually or by a motor 62, e.g. an electric stepping motor 62.

FIG. 3 and FIG. 4 illustrate the jaw thrust mechanism 20, which, in the embodiment shown comprises two drive mechanisms 42 that are connected by a shaft 50 having a handle 38 affixed to one side and gears (not shown inside a housing of the drive mechanisms) that mate with the drive mechanism 42. Rotating handle 38 clockwise or counterclockwise advances or withdraws elongated members 44, which in the embodiment shown are screws in the direction indicated by arrow 46 pushing the mandible engaging elements 18 upwards or lowering them to move the jaw in the direction indicated by arrow 48. In order to be used with subjects having different dimensions, the distance between drive mechanisms 42 can be adjusted as indicated by arrow 52. The button 54 symbolically represents a locking mechanism configured to lock the jaw thrust mechanism 20 to maintain optimal jaw thrust. Other embodiments of the elongated members 44 can comprise other types of mechanical arrangement for raising and lowering mandible engaging elements 18, e.g. a rack and pinion gear. Handle 40 can be rotated either manually or by a motor 62, e.g. an electric stepping motor 62.

Figure 5B:
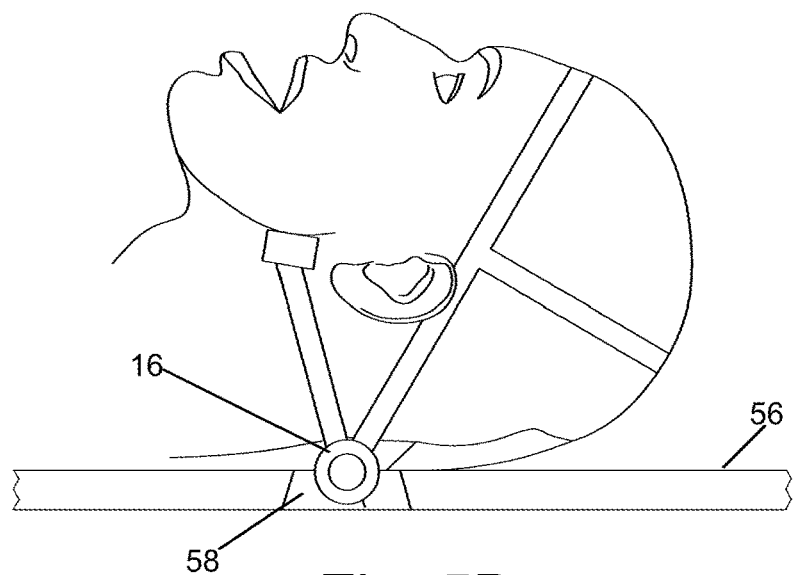
FIG. 5A and FIG. 5B schematically show a device of FIG. 1A attached to a horizontal surface.
Figure 5A:
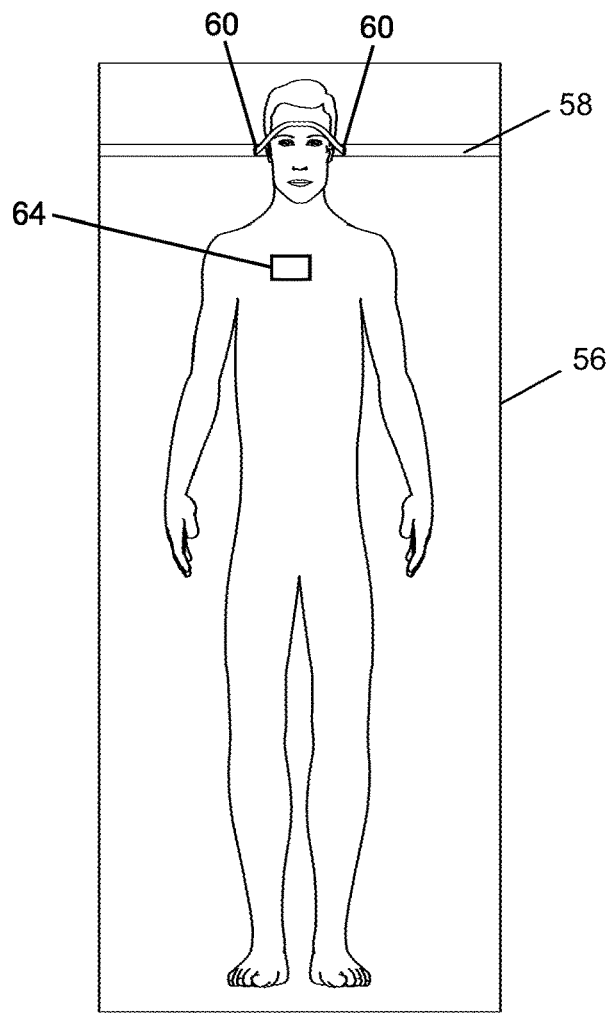

The device may be configured to be attached to a bed a stretcher or any other surface 56 in order to improve the fixation of the patients head as shown in FIG. 5A. The fixation of the head is beneficial in maintaining the required neck angle for optimal opening of the airway which is achieved both by the jaw thrust maneuver and the head tilt. In order to achieve this, the device may include connectors that allow attachment of the device to the surface. In an embodiment the connectors are attached to the device through connection to the neck support portion of the device at each extremity and are configured to be connected to two anchorage points 60, which are positioned on the surface at both sides of the patient's neck. The distance between the two anchorage points 60 on the surface 56 may be adjustable to the size of a patient's neck by allowing their movement on the horizontal axis of the surface 56. This may be achieved by forming the anchorage points 60 on two elements that are configured to be attached to a rail on the surface, e.g. a dovetail rail 58 as shown in FIG. 5B.

The anchorage points 60 may be an integral part of the surface such as in the case of a hospital bed or a stretcher. Alternatively, a universal mounting device is configured to be firmly attached to a flat surface of choice. The universal mounting device comprises two adjustable anchorage points 60 as described above. After attachment of the mounting device to the desired surface the gap between the two anchorage points 60 may be adjusted to the size of a subject's neck. Once adjusted the connectors on the neck support of the head mounted device are connected to the anchorage points 60 on the mounting device in order to achieve fixation of the patient's head to any chosen surface. The device 10 may also include a head support, which is mounted on the surface and supports the distal part of the patient's head. The head support may be a cushion or a rigid element that is connected to the surface either directly or as part of the universal mounting device that is configured to be attached to a flat surface of choice.

As said, the operation of the airway opening mechanism may be manual or may be powered by motors 62. Opening of the airway may be done automatically in response to measurements of the patient's condition by sensors 64 such as pulse oximeter, audio sensors 64 or any other sensor 64 configured to evaluate the state of respiration of the patient and to react to a state of respiratory emergency by automatically opening an airway through optimization of jaw thrust maneuver and/or head tilt.

The intention of the inventors is for the device to be used by an anesthetist to aid in intubation while treating a patient before a surgical procedure, to continue to accompany the patient during the operation and after the operation to preserve an open airway during recovery in the recovery room.

The anesthetist can make use of the device to aid in the process of intubation. The device will be implemented on the patient and secured to the operating table as described herein above. The device fastened to the table will allow the anesthetist by rotating the two handles (30,38) to move the jaw forward (JAW THRUST) and to tilt the head just the amounts needed to position the epiglottis ideally to carry out intubation and to introduce the tube into the trachea.

After the operation and removal of the anesthesia tube the device will maintain the airway of the patient open during the recovery process. After the patient wakes up, the device can be unsecured from the operating table but will remain on him/her until the device is no longer needed to maintain an open airway.

For Ear-Nose-Throat procedures the device can be used not only to aid in intubation but also to prevent movement of the head and the mouth open according to the medical requirements.

The device can also be used to aid in maintaining open upper airways during operations carried out with partial anesthesia, such as in cosmetic surgery. For operations carried out with local anesthesia in which intubation is not required, the device can be used whether fastened or not fastened to the bed. By rotating the handles (30,38) the epiglottis can be positioned to maintain the upper airways open.

Additionally the device can also be used to aid in maintaining open upper airways for patients undergoing examinations, such as MRI and CT and for patients in hospital wards that suffer from breathing problems, such a shortness of breath, apnea, and lung diseases.

Although embodiments of the invention have been described by way of illustration, it will be understood that the invention may be carried out with many variations, modifications, and adaptations, without exceeding the scope of the claims.

The invention claimed is:

1. A wearable device for opening and maintaining an airway in a subject, the device comprising:
   a) a semi-rigid neck support that is positioned behind a neck and is configured to support the neck of the subject,
   b) a head tilt mechanism comprising a handle configured to activate the head tilt mechanism to perform a head tilt maneuver by modifying a head angle of the subject when in a supine position in order to achieve a head tilt position and maintain a head at an optimal angle; and
   c) a jaw thrust mechanism comprising a handle configured to activate the jaw thrust mechanism to perform a jaw thrust maneuver by causing a simultaneous movement of the mandibles on both sides of the head of the subject when in the supine position in order to obtain and maintain an optimal jaw thrust;
   the device characterized in that
   i) the head tilt mechanism comprises: a) a flexible primary strap mechanically connected to the handle, the flexible primary strap configured to be worn on the head of the subject passing over the forehead or over the nose bridge of the subject; b) a pulley to which a first end of the primary strap is affixed; and c) the handle is a rotatable handle mechanically linked to the pulley;
   whereupon activating the handle in a first direction causes a force on one end of the strap that pulls the head downwards or, activating the handle in an opposite direction reduces the force on the strap allowing the head to move upwards;

ii) the head tilt mechanism is affixed to the neck support and the jaw thrust mechanism is attached to the neck support; thereby allowing the device to remain attached to the subject until it is no longer needed to maintain an open airway; and iii) the head tilt mechanism and the jaw thrust mechanism are configured to obtain an optimal opening of the airway, which is achieved by activating the handle of the head tilt mechanism and activating the handle of the jaw thrust mechanism in response to measurements of the subject's condition by sensors configured to evaluate the state of respiration of the subject.

2. The device of claim 1 wherein the device is configured to modify the head angle of the subject and cause a forward movement of the mandibles of the subject in one of: separately or simultaneously.

3. The device of claim 1 wherein the head tilt mechanism comprises:
   a locking mechanism;
   wherein:
   a') the head tilt mechanism is located on one side of the head of the subject;
   b') a second end of the primary strap configured to be firmly affixed to the neck support on the side of the head of the subject opposite to the side at which the head tilt mechanism is affixed to the neck support;
   c') the handle is configured such that rotating it in one of a clockwise or counterclockwise direction exerts a force via a mechanical connection on the pulley wrapping the end of the primary strap around the pulley effectively applying a force via the primary strap that pulls the head downwards and rotating the handle in the opposite direction unwraps the primary strap from around the pulley effectively reducing the force that the primary strap exerts on the head allowing the head to move upwards.

4. The device of claim 3 wherein the head tilt mechanism comprises a secondary strap that is connected to the primary strap and is configured to pass over the top of the head.

5. The device of claim 3 wherein mechanical connection between the handle and the pulley is one of:
   a) a belt; and
   b) a gear train.

6. The device of claim 1 wherein the jaw thrust mechanism comprises:
   a) two drive mechanisms the lower ends of which are configured to be affixed to the neck support on either side of the head of the subject;
   b) a shaft that connects both of the drive mechanisms;
   c) gears that link the drive mechanisms to the shaft;
   d) two elongated members, one projecting upwards from each drive mechanism, the elongated members configured to be raised or lowered in relation to the neck support;
   e) two mandible engaging elements each configured to match the shape of the mandible on a different one of the sides of the head of the subject; and
   f) a locking mechanism configured to lock the jaw thrust mechanism to maintain optimal jaw thrust; wherein:
   i) each of the two mandible engaging elements is pivotally attached to the upper end of a different one of the two elongated members; and
   ii) the handle is configured such that rotating it clockwise or counterclockwise raises or lowers both of the elongated members, thereby pushing the mandible engaging elements upwards or lowering them to move the mandible forwards of backwards; and
   iii) the handle is affixed to one end of the shaft.

7. The device of claim 6 wherein the elongated members are one of: screws or racks from rack and pinion gear assemblies.

8. The device of claim 6 wherein the distance between the two drive mechanisms can be adjusted according to the dimensions of the head of the subject.

9. The device of claim 1 wherein the device is configured to be attached to both the head of the subject and to a bed, stretcher, or other flat surface.

10. The device of claim 9 wherein the neck support comprises connectors configured to attach the device to anchorage points on the bed, stretcher, or other flat surface.

11. The device of claim 1 wherein the handle of the head tilt mechanism and the handle of the jaw thrust mechanism are rotated in one of the following ways: manually or by a motor.

12. The device of claim 11 configured to react to a state of respiratory emergency by automatically opening an airway through activation of the head tilt mechanism and the jaw thrust mechanism in response to measurements of the subject's condition by sensors configured to evaluate the state of respiration of the subject.

* * * * *